United States Patent [19]
Kawai et al.

[11] Patent Number: 5,671,743
[45] Date of Patent: Sep. 30, 1997

[54] DIGITAL ANGIOGRAPHIC APPARATUS

[75] Inventors: Masumi Kawai, Kusatsu; Yuusuke Miura, Kyoto, both of Japan

[73] Assignee: Shimadzu Corporation, Kyoto, Japan

[21] Appl. No.: 642,871

[22] Filed: May 6, 1996

[30] Foreign Application Priority Data

May 22, 1995 [JP] Japan ................... 7-148191

[51] Int. Cl.⁶ ...................................... A61B 6/00
[52] U.S. Cl. ............. 128/654; 378/98.2; 378/98.12
[58] Field of Search ..................... 128/653.1, 654; 378/98.12, 98.2, 98.11, 62; 364/413.23

[56] References Cited

U.S. PATENT DOCUMENTS 4,899,393  2/1990  Morishita et al. .

FOREIGN PATENT DOCUMENTS 0331274  9/1989  European Pat. Off. .
0366075  5/1990  European Pat. Off. .
4417628  9/1995  Germany .

*Primary Examiner*—Ruth S. Smith
*Attorney, Agent, or Firm*—Nikaido, Marmelstein, Murray & Oram LLP

[57] ABSTRACT

A digital angiographic apparatus for reducing exposure of patients to X-ray radiation, and completely eliminating a slip or deviation between mask image and live image. A radiographic image is picked up by emitting X rays through a selected site of a patient injected with a contrast medium. The radiographic image is converted to digital data to obtain a basic image. The basic image is used as a live image retaining high frequency components reflecting blood vessels and the like into which the contrast medium is injected. The basic image is subjected to appropriate frequency processing to remove high frequency components (reflecting the blood vessels and the like), thereby to obtain a mask image. A control unit subtracts the mask image from the live image to obtain a subtraction image extracting a blood vessel image.

13 Claims, 7 Drawing Sheets

DIGITAL ANGIOGRAPHIC APPARATUS

BACKGROUND OF THE INVENTION

1. Field of the Invention

This invention relates to digital angiographic apparatus suited for acquiring subtraction images of one or more sites of a patient.

2. Description of the Related Art

In a conventional practice of acquiring a subtraction image of a site with this type of digital angiographic apparatus, a radiographic image (mask image) is first picked up without injecting the patient with a contrast medium, and then, after injecting a contrast medium, a radiographic image (live image) is picked up of the same site. Subsequently, the mask image is subtracted from the live image.

Subtraction images may be acquired from a plurality of sites, for example, by shifting a positional relationship between the patient and a fluoroscopic device including an X-ray tube and an image pickup system (such as an image intensifier and a television camera) along the body axis of the patient. In this case also, a mask image and a live image are picked up of each site in two separate steps before and after injecting contrast medium.

The conventional apparatus with the above construction has the following drawbacks.

According to the conventional apparatus, the patient is irradiated with X rays each time a mask image or live image is picked up. That is, X-ray irradiation is carried out twice to pick up images of each site. Thus, there remains a problem that a reduction cannot be made in the patient's exposure to X-ray radiation.

Further, the conventional apparatus involves a long interval of time between mask image pickup and live image pickup for each site since the two images are picked up in two separate steps before and after injecting a contrast medium. During this interval, with injection of a contrast medium, the patient is likely to move and cause a slip or deviation between mask image and live image. The resulting subtraction image is vulnerable to artifacts. Such a slip between mask image and live image is more striking where subtraction images are acquired from a plurality of sites by shifting the positional relationship between fluoroscopic device and patient. This is due to mechanical errors of a mechanism for shifting the positional relationship between fluoroscopic device and patient. These mechanical errors entail difficulties in securing, despite control, alignment of a mask image and a live image of the same site.

SUMMARY OF THE INVENTION

This invention has been made having regard to the state of the art noted above, and its object is to provide a digital angiographic apparatus which acquires subtraction images with reduced exposure of patients to X-ray radiation, and which completely eliminates a slip or deviation between mask image and live image.

The above object is fulfilled, according to this invention, by a digital angiographic apparatus for acquiring subtraction images of selected sites of a patient, comprising:
- a fluoroscopic device for irradiating each of the selected sites with X rays, and picking up a radiographic image thereof;
- a data converting device for converting the radiographic image into digital data;
- a high frequency removing device for removing high frequency components from the radiographic image (hereinafter called basic image) picked up of each of the selected sites of the patient injected with a contrast medium, and converted into digital data; and
- a computing unit for deriving a subtraction image from a subtraction between the basic image and an image produced by removing high frequency components from the basic image.

This invention has the following functions.

The fluoroscopic device picks up a radiographic image of a selected site of a patient injected with a contrast medium. The data converting device converts the radiographic image to digital data to obtain a basic image. The basic image includes a background image such as of bones, internal organs and the like as well as an image of blood vessels with the contrast medium flowing therein. The image of blood vessels is an intricate image having intense density variations, i.e. an image containing numerous high frequency components. On the other hand, the background image is a broader and more general image than the blood vessel image, presenting gentle density variations, i.e. an image containing numerous low frequency components. This basic image is used as a live image. The high frequency removing device carries out appropriate frequency processing of the basic image to remove the high frequency components therefrom. The resulting image is without the blood vessel image containing numerous high frequency components, i.e. includes only the background image. This image is used as a mask image. The control unit subtracts the mask image (corresponding to the basic image stripped of the high frequency components) from the live image (basic image) to obtain a subtraction image extracting the blood vessel image.

It will be appreciated that, according to this invention, the patient's exposure to X-ray radiation for obtaining a subtraction image is reduced to a half of what it is in the prior art. This is achieved by obtaining the subtraction image based on a mask image and a live image derived from a radiographic image picked up through a single step of X-ray irradiation.

Further, this invention completely eliminates a slip or deviation between mask image and live image since the two images are derived from a radiographic image picked up through a single X-ray irradiating step. Consequently, the subtraction image is free from artifacts due to such a slip of images.

The high frequency removing device in this invention is not limited to a particular type. For example, this device may identify frequency components forming the basic image through a space-to-frequency conversion, remove high frequency components exceeding a predetermined threshold level, and output the frequency components, with the high frequency components removed therefrom, after a frequency-to-space conversion. Alternatively, the high frequency removing device may remove the high frequency components from the basic image through a filtering process.

The process of removing the high frequency components from the basic image usually involves a time lag. In such a case, the basic image preferably is applied to the computing unit through a delay circuit for causing a delay corresponding to the time lag. This construction compensates for the time lag between the basic image and the image without the high frequency components when applied to the computing unit. Alternatively, the basic image may be stored temporarily in a first storage, and the image without the high frequency components in a second storage, the images being read synchronously from the two storages for application to the computing unit.

The subtraction image provided by the computing unit is displayed on a display device such as a television monitor. Besides, the basic image in the first storage may be displayed on another display device, and the image in the second storage on a further display device. It is also preferred that the subtraction image provided by the computing unit may be stored in a third storage, which may be read and displayed as necessary.

It will be advantageous to enhance the high frequency components of the basic image prior to application as a live image to the computing unit. Then, the computing unit will provide an enhanced subtraction image (extracted image of blood vessels). The digital angiographic apparatus of this invention may include a high frequency enhancing device which increments high frequency components among frequency components of the basic image obtained through a space-to-frequency conversion, and then performs a frequency-to-space conversion thereof.

The apparatus according to this invention may further comprise an integrating device for obtaining a mean image of a plurality of basic images picked up by the fluoroscopic device. After the high frequency components are removed from the mean image of the basic images, the computing unit may perform a subtraction between the mean image and an image produced by removing the high frequency components from the mean image. The resulting subtraction image has a high signal to noise ratio (S/N ratio).

For example, the integrating device may include a gradation converter for carrying out a gradation conversion of densities of the basic images successively obtained through image pickup carried out N times (N being a natural number 2 or more), to reduce the densities to 1/N; an adder for receiving, at one of inputs thereof, the basic images after the gradation conversion by the gradation converter; and a storage for storing and updating added images successively outputted from the adder, and applying a latest one of the added images to the other input of the adder.

Alternatively, the integrating device may include an adder for receiving, at one of inputs thereof, the basic images successively obtained through image pickup carried out N times (N being a natural number 2 or more); a storage for storing and updating added images successively outputted from the adder, and applying a latest one of the added images to the other input of the adder; and a divider for dividing density of the last added image in the storage to be 1/N.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

DETAILED DESCRIPTION OF THE PREFERRED EMBODIMENTS

Preferred embodiments of this invention will be described in detail hereinafter with reference to the drawings.

<First Embodiment>

Figure 1:
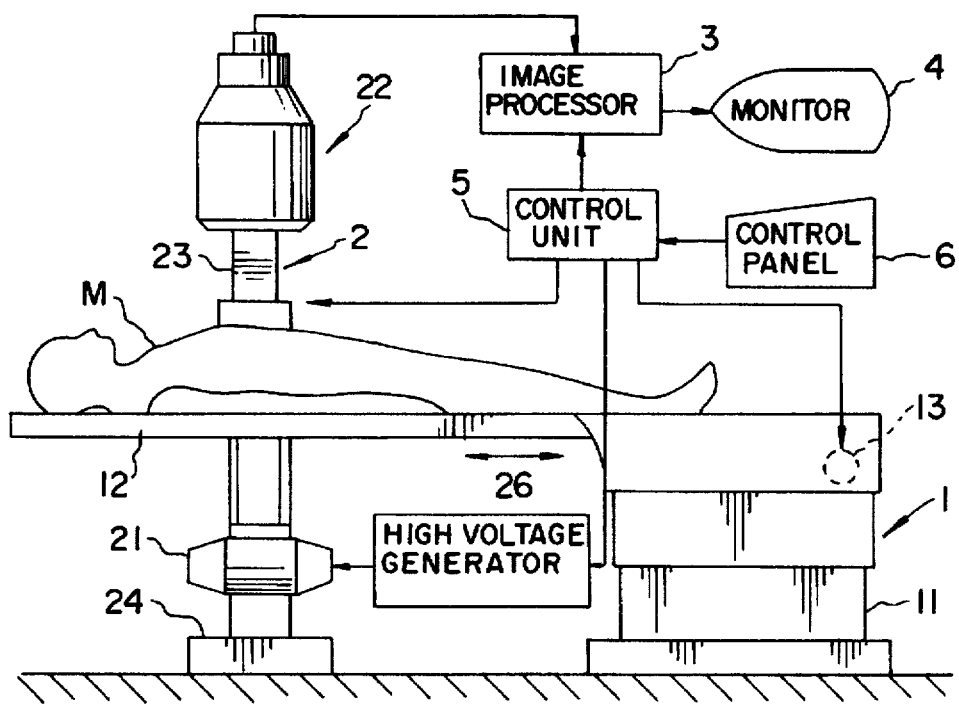
FIG. 1 is an overall front view of a digital angiographic apparatus in a first embodiment of this invention.
Figure 2:
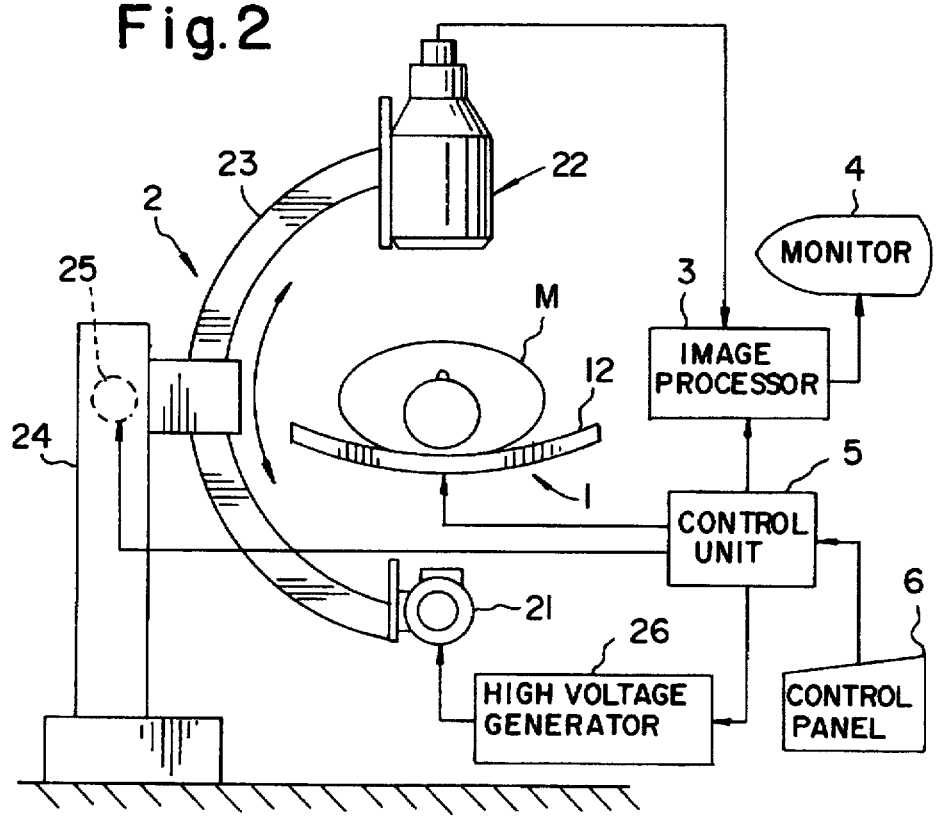
FIG. 2 is a side view showing a fluoroscopic device.
Figure 3:
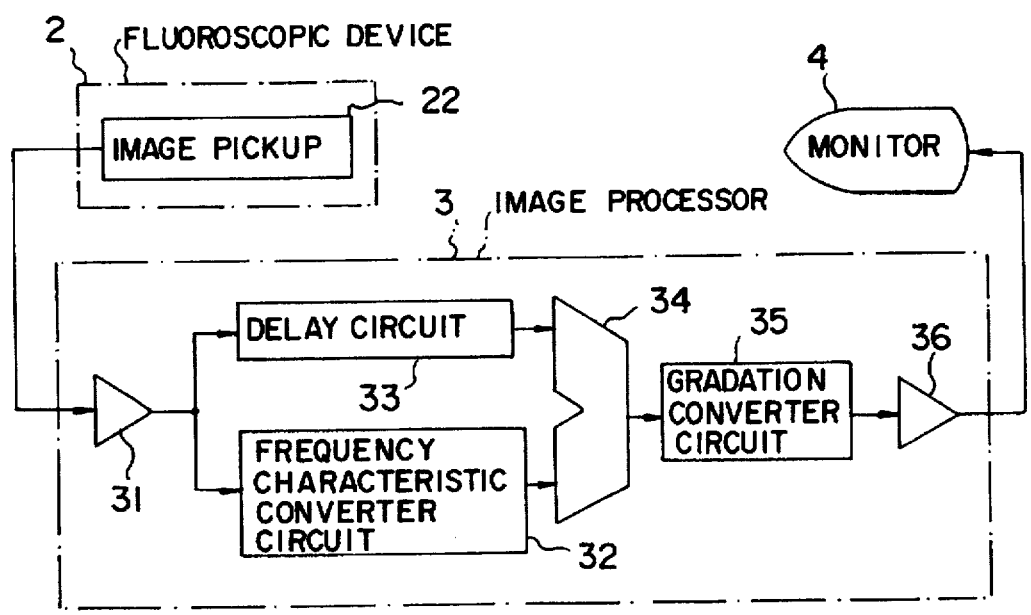
FIG. 3 is a block diagram of an image processor in the first embodiment.

FIG. 1 is an overall front view of a digital angiographic apparatus in a first embodiment of this invention. FIG. 2 is a side view showing a fluoroscopic device. FIG. 3 is a block diagram of an image processor.

The first embodiment includes a bed 1, a fluoroscopic device 2, an image processor 3, a monitor 4, a control unit 5 and a control panel 6.

The bed 1 includes a pedestal 11 installed on a floor, and a top board 12 for supporting a patient M lying thereon. The top board 12 is driven by a motor 13 to move horizontally, thereby to shift a positional relationship between the fluoroscopic device 2 and the patient M on the top board 12 along the body axis of the patient M. The motor 13 is controllable by the control unit 5.

The fluoroscopic device 2 includes an X-ray tube 21 and an image pickup system 22 supported by a C-shaped arm 23. The C-shaped arm 23 is supported by an upper portion of a device column 24 fixed adjacent the bed 1. The C-shaped arm 23 is driven by a motor 25 to be movable in directions indicated by an arrow in FIG. 2. Thus, the X-ray tube 21 and image pickup system 22 are movable about the body axis of patient M, to adjust directions for picking up fluoroscopic images. The motor 25 is controllable by the control unit 5.

The X-ray tube 21 and image pickup system 22 are attached to opposite ends of C-shaped arm 23, and opposed to each other across the patient M lying on the top board 12. The X-ray tube 21 emits X rays to a selected site of patient M, and the image pickup system 22 receives the X rays transmitted through the patient M, thereby to pick up a radiographic image of that site. The X-ray tube 21 emits X rays when predetermined power (X-ray tube voltage and X-ray tube current) is supplied thereto from an X-ray high voltage generator 26. The predetermined power is supplied from the high voltage generator 26 to the X-ray tube 21 under control of the control unit 5. The image pickup system 22 includes an image intensifier and a television camera. The radiographic image picked up is applied to the image processor 3.

As shown in FIG. 3, the image processor 3 includes an A/D (analog-to-digital) converter 31 acting as a data converting device, a frequency characteristic converter circuit 32 acting as a high frequency removing device, a delay circuit 33, a computing unit 34, a gradation converter circuit 35, and a D/A (digital-to-analog) converter 36.

When a radiographic image is picked up of a selected site of patient M injected with a contrast medium, image signals (analog signals) of the image are transmitted from the image pickup system 22 to the A/D converter 31 to be converted to digital data to form a basic image. This basic image includes low frequency components reflecting bones and the like, and high frequency components reflecting blood vessels containing the contrast medium. The basic image is used as a live image. This basic image (live image) is applied to the frequency characteristic converter circuit 32 and delay circuit 33. The frequency characteristic converter circuit 32 removes the high frequency components reflecting the blood vessels and the like from the basic image through a process described hereinafter, to obtain a mask image. The computing unit 34 performs a subtraction between the live image supplied through the delay circuit 33 and the mask image supplied through the frequency characteristic converter circuit 32, and applies a resulting subtraction image to the gradation converter circuit 35. In order to enhance the subtraction image for display on the monitor 5, the gradation converter circuit 35 adjusts densities of pixels (by adding or subtracting predetermined densities to/from the densities of all of the pixels, respectively) forming the subtraction image. The subtraction image with converted gradations is applied to the D/A converter 36 and, after a D/A conversion therein, is displayed on the monitor 4. The delay circuit 33 is provided to compensate for a time lag corresponding to a processing time taken at the frequency characteristic converter circuit 32. Thus, the live image and mask image are synchronously supplied to the computing unit 34. These components of the image processor 3 are operable under control of the control unit 5.

As noted above, the frequency characteristic converter circuit 32 is provided to obtain a mask image by removing the high frequency components reflecting blood vessels and the like from the basic image (live image). If this process, for example, frequency components forming the basic image are identified through a space-to-frequency conversion, the frequency components exceeding a predetermined threshold frequency (i.e. high frequency components) are removed, and the remaining frequency components are subjected to a frequency-to-space conversion to obtain a mask image. This embodiment may employ, as the space-to-frequency conversion, any on of known processes such as FFT (fast Fourier transform), Karhunen-Loeve transform, DCT (discrete cosine transform) and Hadamard transform. The frequency-to-space conversion may be the reverse of the space-to-frequency conversion (i.e. reverse FFT, reverse Karhunen-Loeve transform, reverse DCT or reverse Hadamard transformation). The predetermined threshold frequency may be any frequency empirically determined to be suited for removing blood vessel images.

Chips specially designed to perform, for example, DCT and reverse DCT at high speed (in approximately 1/30 sec.) are commercially available. With use of such a special chip, a subtraction image may be displayed on the monitor 4 in a very short time (almost in real time) after a basic image is picked up.

It is also possible to obtain a mask image without high frequency components forming a blood vessel image, by subjecting a basic image to a template process (e.g. a filtering process to remove the high frequency components).

The control unit 5 controls driving and operations of the various components in response to instructions and the like inputted through the control panel 6. The control unit 5 comprises, for example, a CPU (central processing unit) for executing a program to perform the operation described hereinafter.

The control panel 6 is used by the operator to input sites to be visualized, conditions therefor, start instructions and so on.

The operations of the apparatus having the foregoing construction will be described hereinafter.

First, an operation for acquiring a subtraction image of one site (e.g. the chest) of patient M will be described.

Figure 4:
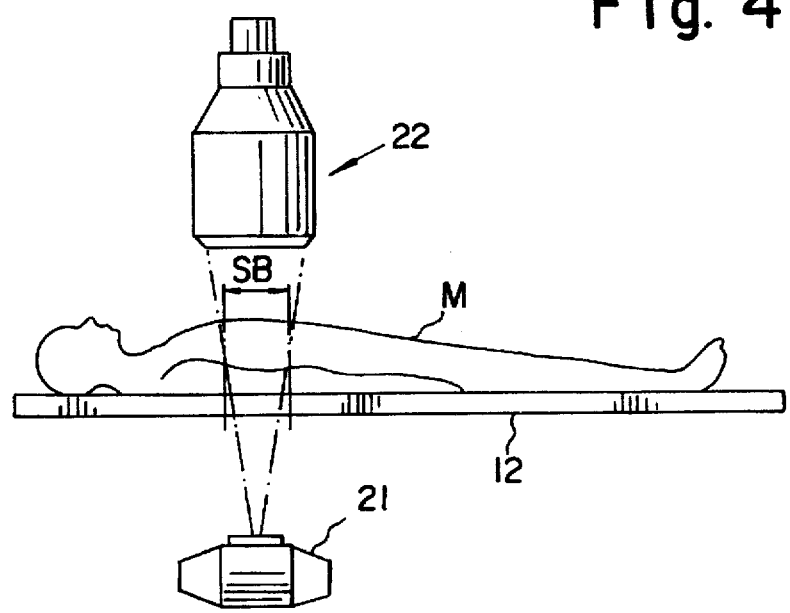
FIG. 4 is an explanatory view of an operation to acquire a subtraction image of a given site.

Based on the site to be visualized and conditions (e.g. a direction of image pickup) therefor determined by the operator through the control panel 6, the control unit 5 drives the motor 13 to move horizontally the top board 12 supporting patient M. Consequently, the selected site (i.e. the chest) is placed in an image pickup position between the X-ray tube 21 and image pickup system 22. Then, the control unit 5 drives the motor 25 to move the X-ray tube 21 and image pickup system 22 about the body axis of patient M (i.e. of the selected site) to adjust the direction of image pickup. This state is shown in FIG. 4. In FIG. 4, the image pickup direction is adjusted such that X rays irradiate selected site SB from below to obtain a radiographic image thereof.

Next, patient M is injected with a contrast medium. It will be appreciated, however, that the above positional adjustment may be carried out after the injection of a contrast medium. In any case, patient M is injected with a contrast medium prior to the image pickup described hereunder. With the contrast medium diffused to the selected site SB, the operator instructs start of the process through the control panel 6 to execute the following image pickup operation.

Upon the instruction to start the process, the control unit 5 controls the X-ray high voltage generator 26 to supply the predetermined power to the X-ray tube 21. The X-ray tube 21 emits X rays to pick up a radiographic image of selected site SB having the contrast medium diffused therein. Then, the control unit 21 controls the various components of the image processor 3 to acquire a basic image (live image), to derive a mask image from the basic image and to perform a subtraction between the live image and mask image, and causes the monitor 4 to display a subtraction image.

According to this embodiment, as described above, it is adequate to irradiate the patient M with X rays once in order to acquire a subtraction image of a given site. The patient's exposure to X-ray radiation is a half of what it is in the prior art. Further, since a mask image and a live image are obtained from a basic image in one frame, a slip between mask image and live image due to movement of the patient is completely eliminated.

Figure 5:
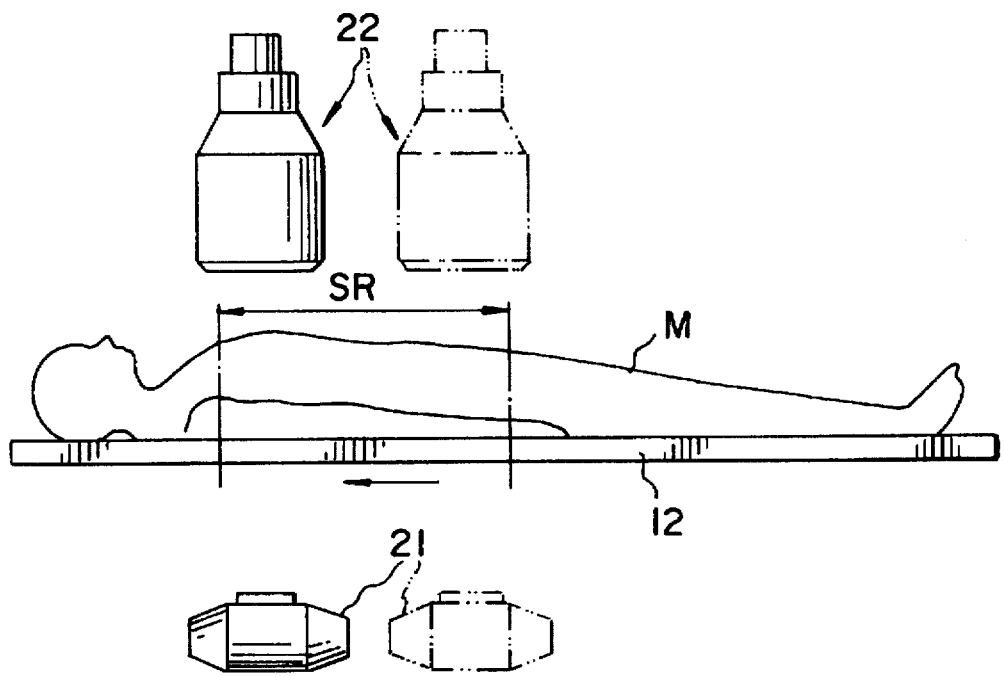
FIG. 5 is an explanatory view of an operation to acquire subtraction images of a plurality of sites along the body axis of a patient.

An operation, as shown in FIG. 5, for acquiring subtraction images of a plurality of sites within a region SR from the chest to the abdomen of patient M will be described next. TMs operation is carried out by shifting the positional relationship between patient M and fluoroscopic device 2 along the body axis of patient M. In this embodiment, the top board 12 supporting patient M is movable horizontally relative to the fixed fluoroscopic device 2. However, to facilitate illustration of the imaging situation, FIG. 5 shows patient M on the top board 12 fixed, with the fluoroscopic device 2 (X-ray tube 21 and image pickup system 22) movable relative thereto.

In this case, the control unit 5 places a first selected site (a leftward portion of the region SR to be visualized, in FIG. 5) in the image pickup position, and adjust the image pickup direction. Then, patient M is injected with a contrast medium prior to the image pickup described hereunder.

With the contrast medium diffused to selected sites (region SR), and on instructions to start the process, a subtraction image is acquired from the first selected site in the same sequence as for acquiring the subtraction image from one selected site SB described hereinbefore. Then, the top board 12 is moved at a constant rate leftward in FIG. 5.

As subsequent selected sites reach the image pickup position, subtraction images are acquired from these sites in succession.

As described above, subtraction images are acquired from a plurality of consecutive sites by shifting the positional relationship between the patient and fluoroscopic device along the body axis of the patient. In this case also, the patient's exposure to X-ray radiation is a half of what it is in the prior art, and a slip between mask image and live image of each site due to movement of the patient or the like is completely eliminated.

This embodiment may be modified to fix the top board 12, with the fluoroscopic device 2 movable along the body axis of patient M on the top board 12, thereby to shift the positional relationship between patient M and fluoroscopic device 2 along the body axis of patient M.

Figure 6:
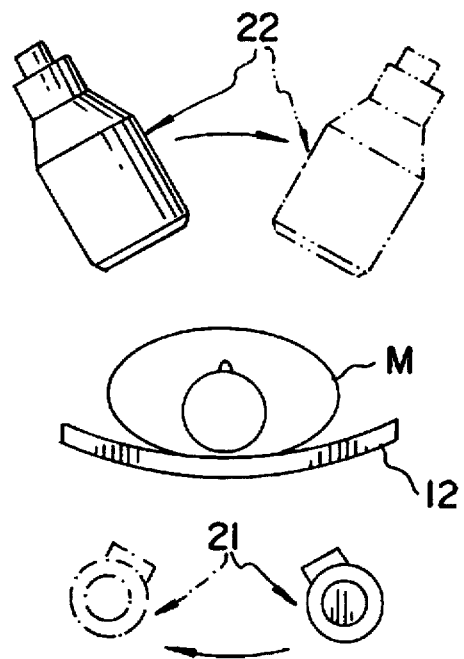
FIG. 6 is an explanatory view of an operation to acquire subtraction images of a given site from a plurality of image pickup directions.

With a given site (e.g. the chest) of patient M placed in the image pickup position, as shown in FIG. 6, the X-ray tube 21 and image pickup system 22 may be revolved about this site (i.e. about the body axis) of patient M to acquire subtraction images from different directions of image pickup. In this case, as in the foregoing operations, the patient is exposed to only a half of the X-ray radiation in the prior art, and no slippage or deviation occurs between a pair of mask image and live image to provide a subtraction image in each image pickup direction.

<Second Embodiment>

Figure 7:
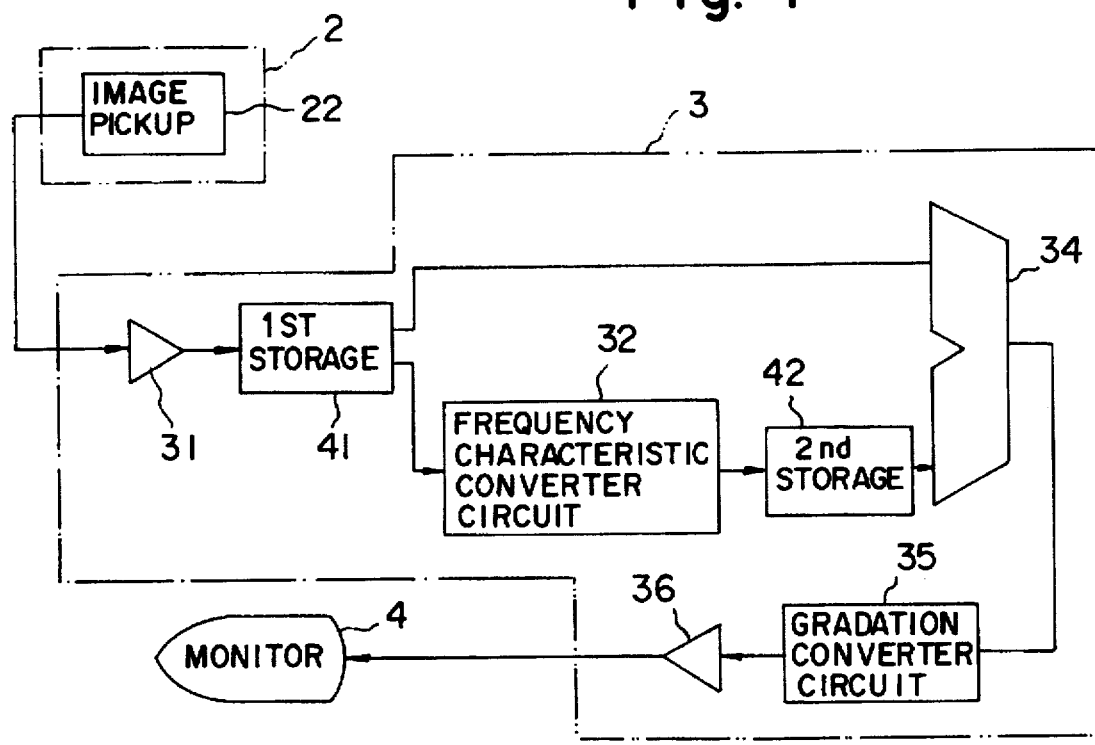
FIG. 7 is a block diagram of an image processor in a second embodiment of the invention.

FIG. 7 is a block diagram of an image processor included in an apparatus in a second embodiment.

In the second embodiment, a basic image (live image) is stored in a first storage 41, and a mask image provided by the frequency characteristic converter circuit 32 is stored in a second storage 42. With this construction, the live image and mask image may be read synchronously from the first and second storages 41 and 42, and applied synchronously to the computing unit 34. Thus, the delay circuit 33 is not needed in the second embodiment.

Where subtraction images are acquired from a plurality of selected sites, or where subtraction images are acquired from a given site in a plurality of image pickup directions, a plurality of live images from the different sites or different directions are stored in the first storage 41, and a plurality of mask images from the different sites or different directions are stored in the second storage 42. After a series of image pickup operations, a subtraction image from a desired site or direction may be selected for display on the monitor 4, for example.

The first and second storages 41 and 42 may be volatile memories or permanent storage media such as magnetic disks. In the latter case, the subtraction images may be displayed at later times.

Figure 8:
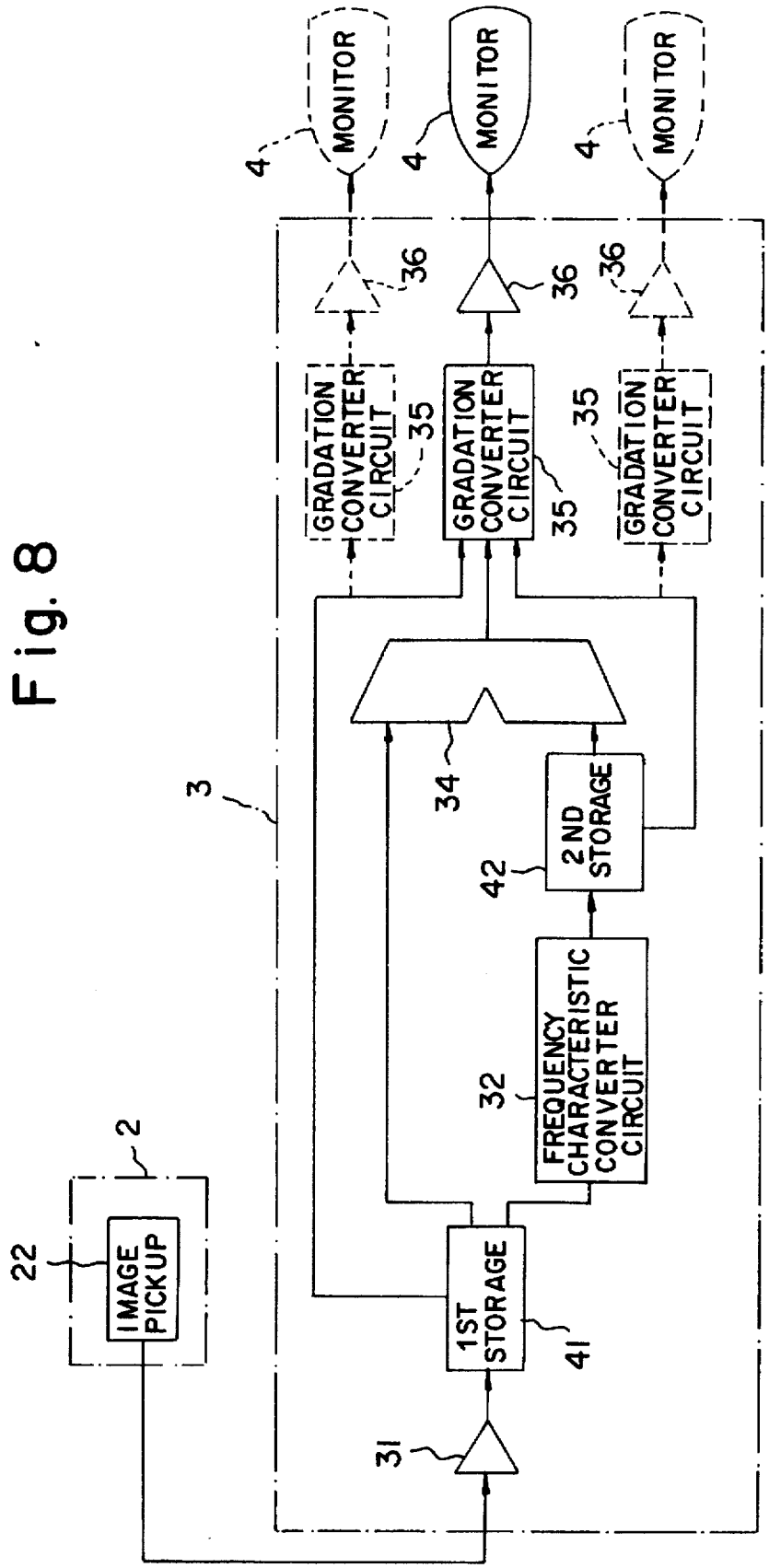
FIG. 8 is a block diagram of a modification of the second embodiment.

In a modified construction as shown in FIG. 8, for example, mask images and live images may be displayed on the monitor 4. Two additional monitors 4 may be provided as shown in dotted lines in FIG. 8. Then, a mask image, a live image and a subtraction image may be displayed in parallel on the respective monitors 4.

Figure 9:
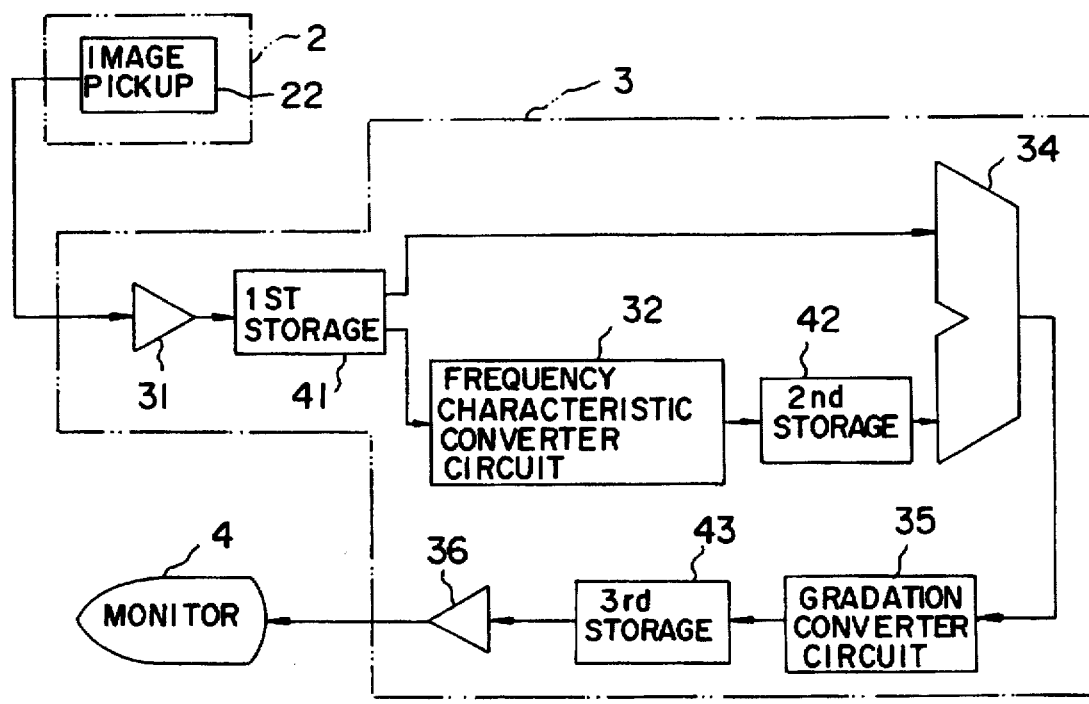
FIG. 9 is a block diagram of another modification of the second embodiment.

As shown in FIG. 9, subtraction images may be stored in a third storage 43. Then, each subtraction image may be displayed repeatedly on the monitor 4 without further computation. The third storage 43 may be a permanent storage medium to enable the subtraction images to be displayed at later times without further computation.

The second embodiment and the modifications thereof may be applied to the third and fourth embodiments described hereinafter.

<Third Embodiment>

Figure 10:
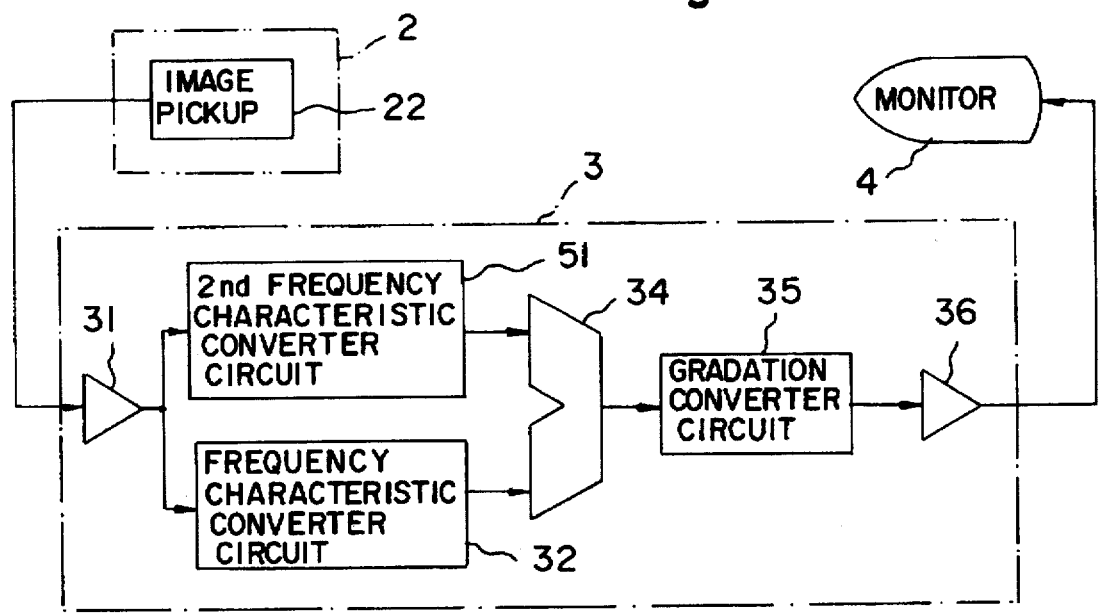
FIG. 10 is a block diagram of an image processor in a third embodiment of the invention.

FIG. 10 is a block diagram of an image processor included in an apparatus in the third embodiment.

The third embodiment is characterized by a second frequency characteristic converter circuit 51 for enhancing high frequency components of basic images (live images).

A process of enhancing the high frequency components of the basic images is achieved, for example, by incrementing the high frequency components among the frequency components of each basic image obtained through a space-to-frequency conversion, and then subjecting these frequency components to a frequency-to-space conversion. The second frequency characteristic converter circuit 51 is constructed to carry out such a process.

This construction provides subtraction images having enhanced images of blood vessels.

The characterizing feature of the third embodiment is applicable also to the fourth embodiment described hereinafter.

<Fourth Embodiment>

Figure 11:
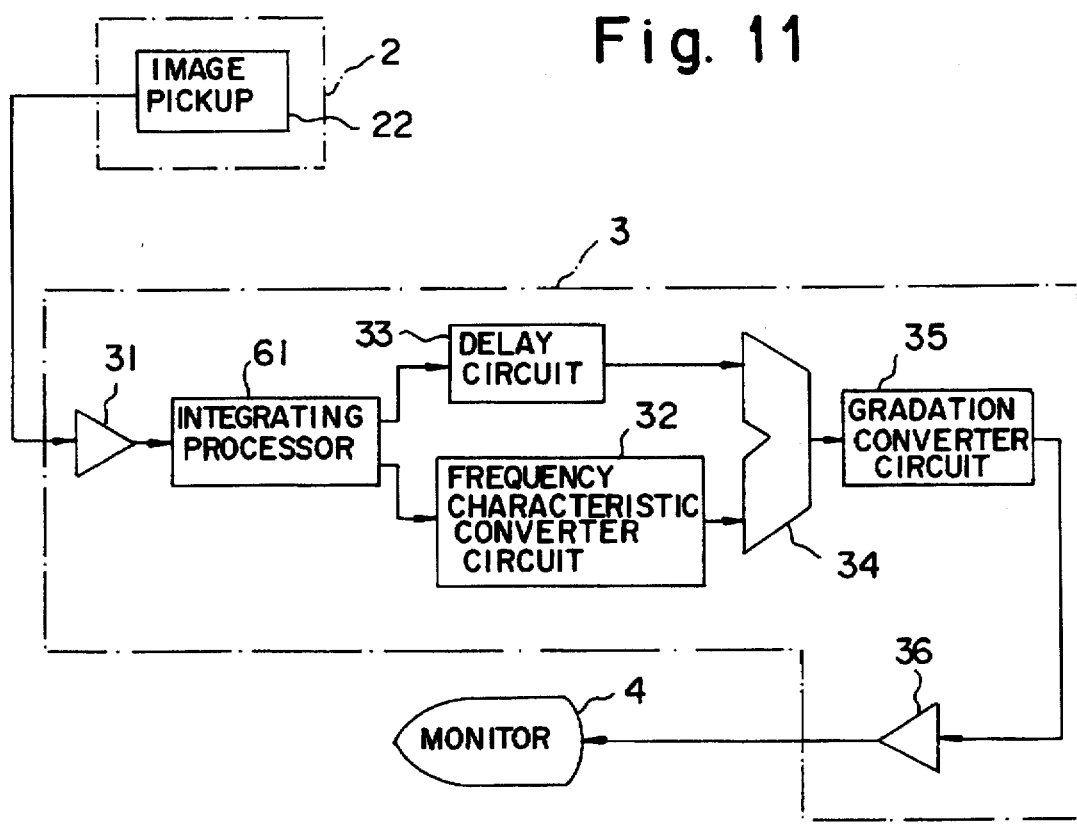
FIG. 11 is a block diagram of an image processor in a fourth embodiment of the invention.

FIG. 11 is a block diagram of an image processor included in an apparatus in the fourth embodiment.

The fourth embodiment is characterized by an integrating processor 61 for deriving a mean image from basic images obtained through a plurality of image pickup steps.

Figure 12A:
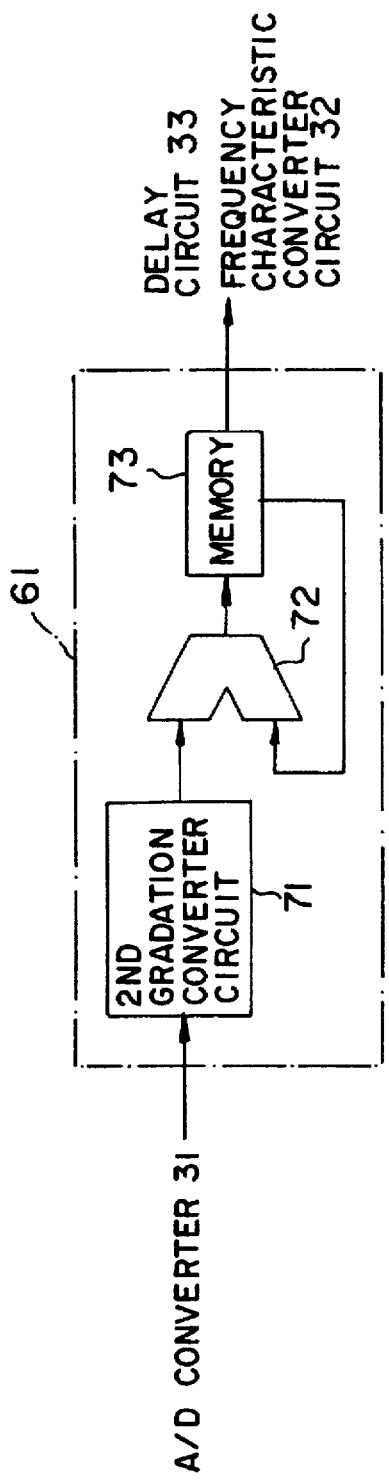
FIGS. 12A and 12B are block diagrams showing examples of integrating processor in the fourth embodiment.

As shown in FIG. 12A, the integrating processor 61 may include a second gradation converter circuit 71, an adder 72 and a memory 73. Alternatively, as shown in FIG. 12B, the integrating processor 61 may include the adder 72, the memory 73 and a divider 74.

Assume, for example, a case of deriving a mean image from basic images obtained through image pickup executed N times. In the construction shown in FIG. 12A, the second gradation converter circuit 71 successively receives densities of the basic images (i.e. densities of pixels in the basic images), and effects a gradation conversion to reduce the densities to 1/N. The adder 72 successively adds the converted densities to images stored in the memory 73. However, nothing is stored in the memory 73 when the first basic image is provided.

Figure 12B:
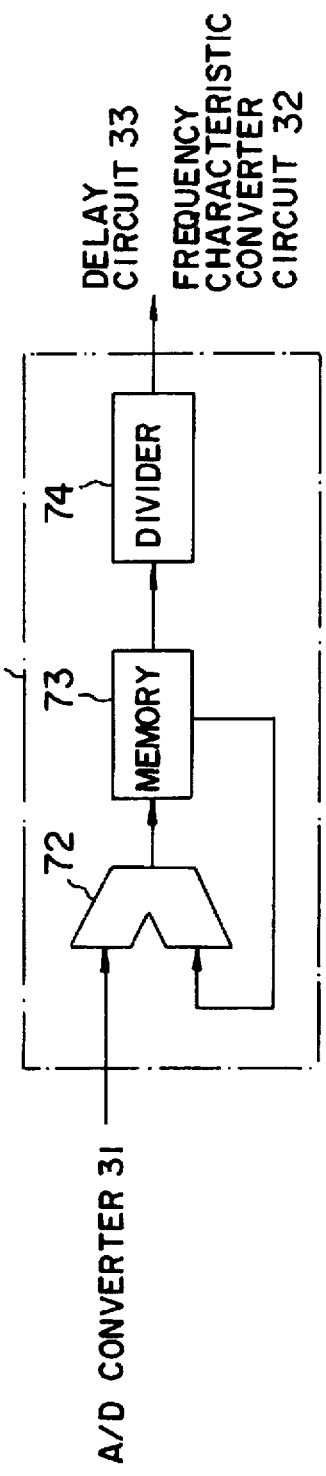

In the construction shown in FIG. 12B, the adder 72 successively receives basic images, and adds these images to images stored in the memory 73 (nothing being stored in the memory 73 when the first basic image is provided). Finally, the divider 74 divides, by N, a sum of the basic images obtained through image pickup executed N times and stored in the memory 73.

The signal to noise ratio of the basic images is improved by determining a mean image of the basic images obtained through image pickup executed N times as described above. Since, in this invention, mask images and live images are derived from the basic images, the signal to noise ratios of the mask images and live images may also be improved all together.

When acquiring a subtraction image of a given site from a single direction of image pickup, basic images are picked up N times by irradiating that site only from the single direction. With the conventional apparatus, mask images and live images may be picked up a plurality of (N) times, respectively, to derive mean images thereof in order to improve the S/N ratios of the mask images and live images. In this case, the patient is exposed to X-ray radiation twice N times since the mask images and live images are picked up separately. In this embodiment, the patient's exposure to X-ray radiation is only a half of what it is in the prior art.

When acquiring subtraction images from a plurality of selected sites by shifting the positional relationship between patient and fluoroscopic device along the body axis of the patient, a mean image of each site may be derived from a plurality of basic images picked up of adjacent sites preceding and following that site. When acquiring subtraction images from a plurality of image pickup directions by revolving the X-ray tube and image pickup system about a given site, a mean image of that site in each direction may similarly be derived from a plurality of basic images picked up in adjacent directions preceding and following that direction. In these cases also, the patient is exposed to a half of the X-ray radiation in the prior art (when the conventional apparatus is used to acquire mean images in similar sequences).

The present invention may be embodied in other specific forms without departing from the spirit or essential attributes thereof and, accordingly, reference should be made to the appended claims, rather than to the foregoing specification, as indicating the scope of the invention.

What is claimed is:

1. A digital angiographic apparatus for acquiring subtraction images of selected sites of a patient, comprising:

fluoroscopic means for irradiating each of said selected sites with X rays, and picking up a radiographic image thereof;

data converting means for converting said radiographic image into digital data;

high frequency removing means for removing high frequency components from said radiographic image (hereinafter called basic image) picked up of each of said selected sites of the patient injected with a contrast medium, and converted into digital data; and computing means for deriving a subtraction image from a subtraction between said basic image and an image produced by removing high frequency components from said basic image.

2. An apparatus as defined in claim 1, wherein said high frequency removing means is operable to identify frequency components forming said basic image through a space-to-frequency conversion, remove high frequency components exceeding a predetermined threshold level, and output said frequency components, with said high frequency components removed therefrom, after a frequency-to-space conversion.

3. An apparatus as defined in claim 1, wherein said high frequency removing means is operable to remove high frequency components from said basic image through a filtering process.

4. An apparatus as defined in claim 1, further comprising a delay circuit for receiving said digital data of said radiographic image from said data converting means, said delay means applying said digital data to said computing means with a delay corresponding to a time lag due to processing by said high frequency removing means.

5. An apparatus as defined in claim 1, further comprising first storage means for storing said basic image outputted from said data converting means, and second storage means for storing an image produced by removing high frequency components from said basic image by said high frequency removing means, said computing means synchronously reading said basic image and said image from said first and second storage means.

6. An apparatus as defined in claim 1, further comprising display means for displaying said subtraction image provided by said computing means.

7. An apparatus as defined in claim 5, further comprising display means for displaying said basic image stored in said first storage means, display means for displaying said image stored in said second storage means, and display means for displaying said subtraction image provided by said computing means.

8. An apparatus as defined in claim 1, further comprising third storage means for storing said subtraction image provided by said computing means.

9. An apparatus as defined in claim 1, further comprising high frequency enhancing means for enhancing high frequency components of said basic image provided by said data converting means, said computing means deriving a subtraction image of said selected site from a subtraction between said basic image, with said high frequency components enhanced by said high frequency enhancing means, and an image produced by removing said high frequency components from said basic image.

10. An apparatus as defined in claim 9, wherein said high frequency enhancing means is operable to increment high frequency components among frequency components of said basic image obtained through a space-to-frequency conversion, and then to output said high frequency components after a frequency-to-space conversion.

11. An apparatus as defined in claim 1, further comprising integrating means for obtaining a mean image of a plurality of basic images picked up by said fluoroscopic means, said high frequency removing means removing high frequency components from said mean image provided by said integrating means, said computing means deriving a subtraction image of said selected site from a subtraction between said mean image and an image produced by removing said high frequency components from said mean image.

12. An apparatus as defined in claim 11, wherein said integrating means includes:

gradation converting means for carrying out a gradation conversion of densities of said basic images successively obtained through image pickup carried out N times (N being a natural number 2 or more), to reduce said densities to 1/N;

adding means for receiving, at one of inputs thereof, said basic images after said gradation conversion by said gradation converting means; and storage means for storing and updating added images successively outputted from said adding means, and applying a latest one of said added images to the other input of said adding means.

13. An apparatus as defined in claim 11, wherein said integrating means includes:

adding means for receiving, at one of inputs thereof, said basic images successively obtained through image pickup carried out N times (N being a natural number 2 or more);

storage means for storing and updating added images successively outputted from said adding means, and applying a latest one of said added images to the other input of said adding means; and dividing means for dividing density of the last added image in said storage means to be 1/N.

* * * * *